United States Patent [19]

Hirsbrunner

[11] Patent Number: 4,839,179
[45] Date of Patent: Jun. 13, 1989

[54] PREPARATION OF A COMPOSITION BASED ON A FINELY DIVIDED ACTIVE PRINCIPLE OF LOW WATER SOLUBILITY

[75] Inventor: Pierre Hirsbrunner, Les Monts-de-Corsier, Switzerland

[73] Assignee: Nestec S. A., Vevey, Switzerland

[21] Appl. No.: 206,910

[22] Filed: Jun. 10, 1988

Related U.S. Application Data

[63] Continuation of Ser. No. 832,167, Feb. 20, 1986, abandoned.

[30] Foreign Application Priority Data

Mar. 20, 1985 [CH] Switzerland ............... 1235/85

[51] Int. Cl.$^4$ ............... A23C 9/154; A23C 9/18; A23C 9/156
[52] U.S. Cl. ............... 426/98; 426/580; 426/584; 426/588; 426/285; 424/439
[58] Field of Search ............ 426/98, 289, 285, 580, 426/587, 588, 584; 424/439–442

[56] References Cited

U.S. PATENT DOCUMENTS

| | | | |
|---|---|---|---|
| 3,591,584 | 0/1971 | Lombardino . | |
| 3,591,854 | 0/1971 | Cole . | |
| 3,928,560 | 12/1975 | Neely et al. | 426/548 |
| 4,358,464 | 11/1982 | Soehnlen | 426/41 |
| 4,427,701 | 1/1984 | Morley | 426/36 |

OTHER PUBLICATIONS

Merck Index, pp. 1082 and 1309.

*Primary Examiner*—Marianne Cintins
*Attorney, Agent, or Firm*—Vogt & O'Donnell

[57] ABSTRACT

A process for the preparation of a composition based on a finely divided active principle sparingly soluble in water and intended to be dispersed in water without forming a deposit. The active principle is mixed in a quantity of from 0.4 to 10% with non-fat milk solids, preferably skimmed milk powder, and the particles of said mixture are subjected to movement at a temperature above 40° C., but at a temperature at which the non-fat milk solids do not burn, for a time sufficient for at least partially encapsulating the particles with the non-fat milk solids.

23 Claims, 2 Drawing Sheets

PREPARATION OF A COMPOSITION BASED ON A FINELY DIVIDED ACTIVE PRINCIPLE OF LOW WATER SOLUBILITY

This is a continuation of application Ser. No. 06/832,167, filed on Feb. 20, 1986, now abandoned.

BACKGROUND OF THE INVENTION

This invention relates to a process for the preparation of a composition based on a finely divided active principle sparingly soluble in water and intended to be dispersed in water without forming a deposit.

The deposition or sedimentation of an active principle substantially insoluble in water during reconstitution in water is a well-known problem. It is also a particularly acute problem, above all, in the case of medicaments. This is because the patient wishing to take a medicament has to follow the posology of the doctor treating him or her. If, during reconstitution in water, part of the active principle remains at the bottom of the glass and if the operation is repeated several times a day, there is a considerable risk of ineffectuality of the treatment envisaged. Various solutions have been proposed with a view to overcoming this problem. For example, emulsifiers or dispersants are added to pharmaceutical or nutritive compositions of the type in question to facilitate suspension of the active principle. However, the inclusion of additives such as these is not always permitted by law so that the composition of the preparations differs according to the countries where they are to be marketed. On the other hand, such additions increase the price of the preparation in question.

SUMMARY OF THE INVENTION

The process according to the present invention enables the disadvantage of incorporating an additional substance in a composition intended for dispersion in water to be eliminated whilst at the same time improving said dispersibility in water.

The present invention relates to a process for the preparation of a composition based on a finely divided active principle sparingly soluble in water and intended to be dispersed in water without forming a deposit, in which the active principle is mixed in a quantity of from 0.4 to 10% by weight with non-fat milk solids, preferably skimmed milk powder, and in which the particles of said mixture are subjected to movement at a temperature above 40° C.

According to the invention, concomitance between the movement of the particles of the mixture and the heat treatment is essential.

DESCRIPTION OF PREFERRED EMBODIMENTS

Figure 1:
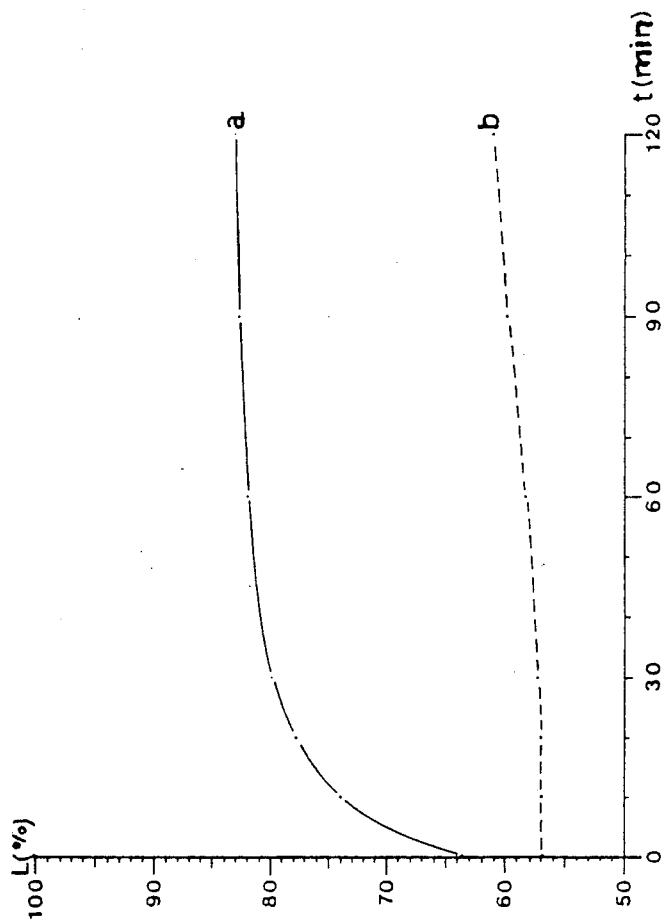

The water-insoluble active principle treated is not critical. It may be any powder-form substance substantially insoluble in water and usable in the form of a dispersion in water. This may be a pharmaceutical active principle or a compound usable for nutritive purposes. Pharmaceutical active principles include, in particular, systemic anti-inflammatories, such as thiazine derivatives according to German patent application DE-OS 25 37 070 disclosing thiazine and thienothiaine derivatives of the general formula:

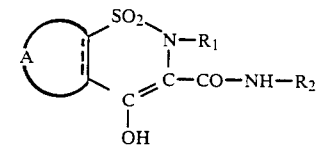

wherein A and the carbon atoms having having the double bond denoted by the dotted line of the formula comprise a group selected from the group consisting of

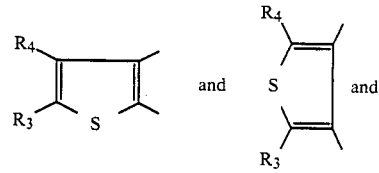

wherein $R_1$ is a lower alkyl, wherein $R_2$ is a residue of an aromatic heterocyclic group selected from the group consisting of an aromatic heterocyclic group having 1 to 4 heterocyclic atoms and an aromatic heterocyclic having 1 to 4 heterocyclic atoms substituted by at least one group selected from the group consisting of a lower alkyl group, a phenyl residue and a phenyl residue substituted by at least one group selected from the group consisting of a halogen, a hydroxy, a lower alkyl, trifluoromethyl and a lower alkoxy, and wherein $R_3$ and $R_4$ are selected from the group consisting of a hydrogen atom and a lower alkyl, particularly the product known as TENOXICAM, 4-Hydroxy-2-methyl-N-2-pyridinyl-2H-thieno[2,3-e]-1,2-thiazine-3-carboxamide 1,1 dioxide and its homologs, or those according to U.S. Pat. No. 3,591,584, disclosing benzothiazine dioxide derivatives of 3,4-dihydro-4-oxo-2H-1,2-benzothiazine-3-carboxamide 1,1 dioxides and 3,4-dihydro-dihydro-3-oxo-2H-1,2-benzothiazine-4-carboxamide 1,1 dioxides, particularly PIROXICAM, 3,4-dihydro-2-methyl-4-oxo-N-2-pyridyl-2H-1,2-benzothiazine-3-carboxamide 1,1 dioxide and its homologs.

The nutritive active principle used in accordance with the invention is preferably cocoa or carob bean.

In the context of the invention, finely divided is understood to mean particles ranging from about 0.2 to 40 microns in size.

The problem of sedimentation of sparingly water-soluble products is further aggravated if products of high specific gravity are used. This is particularly the case with TENOXICAM. The active principle sediments to the bottom of the container more quickly, further increasing the risks of wrong posology. In addition, with a pharmaceutical active principle, it is known that this can cause gastric disorders in patients. Milk powder has already been proposed to reduce this incompatibility, instant skimmed milk powder having a water content of from 2 to 4% preferably being used.

The temperature at which the particles of the mixture are subjected to movement is critical in the process according to the invention. This is because, if the temperature is too low, there is no "trapping" or "adsorption" of the active principle by the milk powder. On the other hand, if the temperature is too high, it promotes "burning" of the milk powder. The treatment temperature is preferably in the range of from 60° to 90° C.

When cocoa is the active principle, the entire quantity of instant skimmed milk powder is preferably mixed directly with the cocoa. In that case, from 5 to 10% by weight of cocoa is mixed with the milk powder.

When the active principle is a pharmacologically active substance, it is mixed in a quantity of from 0.4 to 10% by weight with the milk powder and skimmed milk powder is then added so as to obtain a concentration of active principle of from 0.1 to 1% by weight.

This embodiment of the process according to the invention is carried out in two steps. In the first step, the active principle is mixed with part of the milk powder and the resulting mixture is subjected to the heat treatment. In the second step, the rest of the milk powder is added to obtain the desired concentration of active principle.

It is obvious that the embodiment for the nutritive active principle may be envisaged for the pharmaceutical active principle and vice versa.

Besides the heat treatment, it is important according to the invention to subject the particles of the mixture to movement. The particles are subjected either to a sudden and rapid treatment or a long and gentle treatment for a time sufficient for at least partially encapsulating the particles of the particulate composition in the mixture with the non-fat milk solids.

In the first embodiment, the particles of the mixture are moved by mechanical means, preferably in the form of an electrical blade mill, for example, by an electrical mixer. This treatment lasts for 15 to 120 seconds. In view of the heating of the motor, the mixture simultaneously undergoes a heat treatment at a temperature of from 60° to 90° C.

In the second embodiment, the mixture is moved by agitation means, for example, by a magnetic agitator. In this case, the mixture of particles is placed in a water bath at a temperature of from 50° to 80° C. and the treatment lasts for 15 to 120 minutes.

When the process according to the invention is applied, a powder is obtained in which the milk particles have at least partially encapsulated the active substance, thus making it possible during reconstitution in water to obtain a suspension which remains sufficiently stable for longer than the period of time envisaged for ingestion of said suspension. It may also be added that the powder obtained may readily be stored for as long a period as the milk powder alone.

The present invention also relates to the product obtained by the process described above. This product is in the form of a powder or tablets. In the case of a nutritive active principle, preference is attributed to the powder form whereas, in the case of the pharmaceutical active principle, the product is preferably in tablet form.

Irrespective of whether the product is in powder or tablet form, it may also contain any additive known in the art, for example, flavorings, sweeteners, such as sugars, aspartame and others or any of the known excipients usable in pharmaceutical compositions, such as those used for example in anti-inflammatory compositions. These additives may be used in the quantities in which they are normally used in the art.

EXAMPLES AND DESCRIPTION OF DRAWINGS

Figure 2:
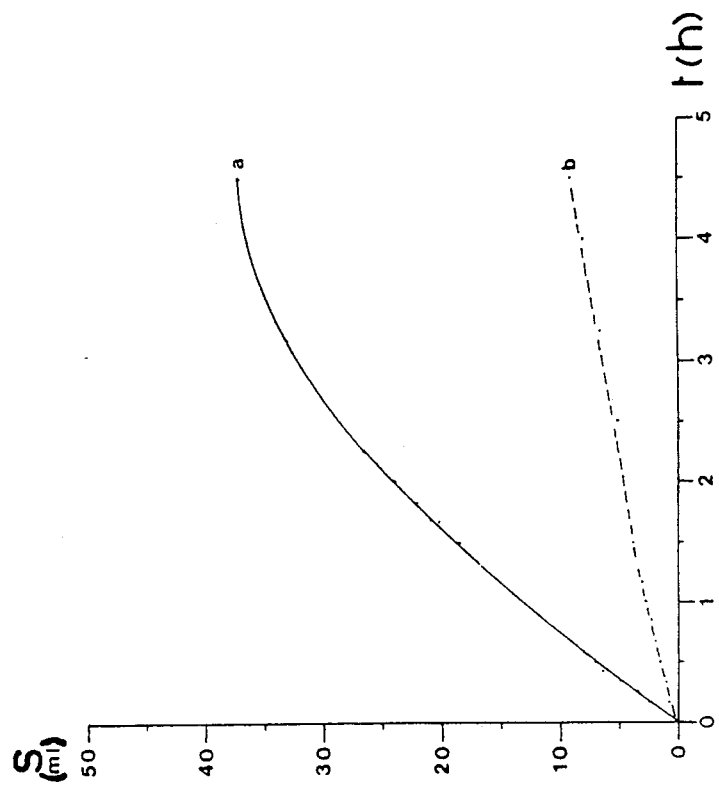

The process according to the invention is illustrated by the following Examples in conjunction with the accompanying drawings in which FIGS. 1 and 2 represent sedimentation as a function of time as analyzed with a spectrocolorimeter and by the Imhof test.

EXAMPLE 1

27 g of instant skimmed milk powder are introduced with 3 g of cocoa powder containing 17% lipids into a high-speed electrical blade mill. After 90 seconds operation, the temperature of the powder is 82° C. The primary structure of the milk powder, although greatly modified, provides for rapid dissolution in water and imparts to the cocoa the ability to remain suspended for a much longer time than in the reference, as discussed below.

To demonstrate this, a sedimentation test is carried out using a spectrocolorimeter. The principle of this test is based on measurement of the light intensity of a reflected light beam after having passed through the sample to be studied.

The factor L denotes this reflected light intensity. The spectrocolorimeter used, namely a "PYE-UNICAM"Mod. SP-8/100, is calibrated with whole milk which is given the value $L=100\%$. The value $L=0$ would be the total absence of reflection, namely with a black body. The incident beam has a wavelength of 546 nm.

FIG. 1 shows the variation of the factor L as a function of time for the reference (curve a) and according to Example 1 (curve b). The reference comprises 10% cocoa cold-mixed with instant skimmed milk powder. The mixture according to the present Example contains the same amount of cocoa, but treated in accordance with the invention. A low value L means that the particles are in suspension whereas a high L value indicates sedimentation.

A rapid increase in L can clearly be seen for the reference whereas the factor L varies only very slightly for the sample according to Example 1. In the first case, therefore, there is rapid sedimentation of the cocoa whereas, for the sample according to the invention, there is very little sedimentation after two hours.

The Imhof test also enables the sedimentation of a suspended product to be demonstrated. In this case, 100 g of dry matter are mixed with 900 ml of water and the sedimentation S in ml is studied in a drawn-out test tube. FIG. 2 shows the results of this test for the reference (curve a) and for the sample according to the invention (curve b). The difference is very clear: the reference shows a sedimentation of 40% after 5 hours whereas the sample according to the invention shows only 10% sedimentation after the same period.

EXAMPLE 2

90 g of instant skimmed milk powder and 10 g of cocoa powder are simultaneously introduced into a glass container equipped with a magnetic agitator which is subjected to a rotational speed of 180 r.p.m. The whole is thermostatically controlled in a water bath at 60° C. agitated under the described conditions for 20 minutes.

The product thus obtained has virtually retained its structure although, during reconstitution in water, the insoluble cocoa is kept in suspension as in Example 1.

EXAMPLE 3

3 g of TENOXICAM, 4-Hydroxy-2-methyl-N-2-pyridinyl-2H-thieno[2,3-e]-1,2-thiazine-3-carboxamide 1,1 dioxide are treated with 27 g of instant skimmed milk powder under the conditions described in Example 1. After 90 seconds treatment, the temperature is 85° C. and an extremely homogeneous and fine powder is obtained. Dry mixing of 4 g of this powder with 96 g of instant skimmed milk powder gives a yellow/cream colored granular preparation containing 20 mg of TENOXICAM per 5 g dose (therapeutic dose) with the property of perfect stability of the suspension during dispersion of the preparation in water. The bitterness induced by the intense dispersion of the bitter active principle may be reduced by using aspartame (25 mg/dose), flavoring (vanillin 10 mg/dose) and approx. 1% of gelatinizing agent (Hercules Powders carboxymethylcellulose). In the untreated reference, 45% of the TENOXICAM has sedimented 15 mins. and 95% 20 mins. after suspension in water.

EXAMPLE 4

8 g of "PIROXICAM", 3,4-dihydro-2-methyl-4-oxo-N-2-pyridyl-2H-1,2-benzothiazine-3-carboxamide 1,1 dioxide (particle size between 0.2 and 4μ) 35 were introduced into a glass reactor with 92 g of instant skimmed milk powder. After treatment for 20 minutes with gentle magnetic agitation (as in Example 2) in a water bath at 70° C., a heavily colored granular mixture is obtained and, after dilution by ordinary dry-mixing in 600 g of instant skimmed milk powder and 300 g of casein condensed with formol ("PLASVITA", a product of "DYNAMIT NOBEL"), is tabletted by the usual methods, one 2.5 g tablet containing 20 mg of finely dispersed active principle.

Contacting the tablet with water results in rapid dispersion and the colored active principle does not sediment, even after a prolonged period. A sweetener and a flavoring are used as in Example 3.

In all the above Examples, the water content of the instant skimmed milk powder was 3.5%.

I claim:

1. A process for treating particles of a particulate composition, wherein the particles of the composition are substantially insoluble in water but are dispersible in water and range in size from about 0.2 microns to about 40 microns, for improving dispersion of the particles in water for obtaining a suspension of the particles in water comprising mixing the particles of the particulate composition with non-fat milk solids powder in an amount for obtaining a concentration of the particulate composition in an amount of from 0.4% to 10% by weight, and moving the mixture at a temperature above 40° C., but at a temperature at which the non-fat milk solids do not burn, for a time sufficient for at least partially encapsulating the particles of the particulate composition in the mixture with the non-fat milk solids powder.

2. A process as claimed in claim 1 wherein the temperature is from 60° C. to 90° C.

3. A process as claimed in claim 1 wherein the non-fat milk solids have a water content of from 2% to 4%.

4. A process as claimed in claim 1 wherein the non-fat milk solids powder is skimmed milk powder.

5. A process as claimed in claim 1 wherein the mixing is by mechanical means such that the temperature of above 40° C. is developed by the mechanical means.

6. A process as claimed in claim 5 wherein the mixing is by an electrical blade mill for from 15 to 120 seconds.

7. A process as claimed in claim 1 wherein the particles and non-fat milk solids powder are heated and agitated for from 15 to 120 minutes.

8. A process as claimed in claim 1 wherein the particulate composition is cocoa.

9. A process as claimed in claim 8 wherein the cocoa is mixed with the non-fat milk solids powder to obtain a concentration of the cocoa in an amount of from 5% to 10% by weight.

10. A process as claimed in claim 1 wherein the particulate composition is pharmacologically active.

11. A process as claimed in claim 10 further comprising, after treating the particles for at least partially encapsulating the particles with the non-fat milk solids powder, adding and combining skimmed milk powder to the mixture for obtaining a concentration of the particulate composition in an amount of from 0.1% to 1% by weight.

12. A process as claimed in claim 10 wherein the particulate composition is a systemic anti-inflammatory.

13. A process as claimed in claim 10 wherein the particulate composition is selected from the group consisting of 3,4-dihydro-4-oxo-2H-1,2-benzothiazine-3-carboxamide 1,1-dioxides and 3,4-dihydro-3-oxo-2H-1,2-benzo-thiazine-4-carboxamide 1,1 dioxides.

14. A process as claimed in claim 10 wherein the particulate composition is selected from the group consisting of 3,4-dihydro-2-methyl-4-oxo-N-2-pyridyl-2H-1,2-benzothiazine-3-carboxamide 1,1 dioxide and homologs thereof.

15. A process as claimed in claim 10 wherein the particulate composition is selected from the group consisting of thiazine and thienothiazine derivatives of the general formula:

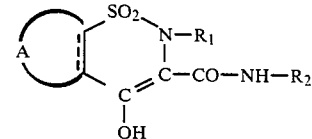

wherein A and the carbon atoms having having the double bond denoted by the dotted line of the formula comprise a group selected from the group consisting of

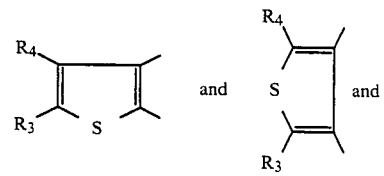

wherein $R_1$ is a lower alkyl, wherein $R_2$ is a residue of an aromatic heterocyclic group selected from the group consisting of an aromatic heterocyclic group having 1 to 4 heterocyclic atoms and an aromatic heterocyclic group having 1 to 4 heterocyclic atoms substituted by at least one group selected from the group consisting of a lower alkyl group, a phenyl residue and a phenyl residue substituted by at least one group selected from the group consisting of a halogen, a hydroxy, a lower alkyl, trifluoromethyl and a lower alkoxy, and wherein $R_3$ and $R_4$ are selected from the group consisting of a hydrogen atom and a lower alkyl.

16. A process as claimed in claim 10 wherein the particulate composition is selected from the group consisting of 4-Hydroxy-2-methyl-N-2-pyridinyl-2H- thieno[2,3-e]-1,2 thiazine-3-carboxamide 1,1-dioxide and homologs thereof.

17. A process as claimed in any one of claims 13–16 further comprising, after mixing the non-fat milk solids powder and the particulate composition, adding and combining skimmed milk powder to the mixture to obtain a concentration of the particulate composition of from 0.1% to 1% by weight.

18. The product of the process of claim 1.
19. The product of the process of claim 8.
20. The product of the process of claim 10.
21. The product of the process of claim 9.
22. The product of the process of any one of claims 11 or 12 or 13 or 14 or 15 or 16.
23. The product of any one of claims 18–20 wherein the non-fat milk solids powder is skimmed milk powder.

* * * * *